(12) United States Patent
Khurshid et al.

(10) Patent No.: US 11,805,995 B1
(45) Date of Patent: Nov. 7, 2023

(54) SALIVA COLLECTION KIT

(71) Applicant: KING FAISAL UNIVERSITY, Al-Ahsa (SA)

(72) Inventors: Zohaib Khurshid, Al-Ahsa (SA); Mohammed Farhan Alfarhan, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 14 days.

(21) Appl. No.: 17/992,608

(22) Filed: Nov. 22, 2022

(51) Int. Cl.
*A61B 5/00* (2006.01)
*A61B 10/00* (2006.01)

(52) U.S. Cl.
CPC .................. *A61B 10/0051* (2013.01)

(58) Field of Classification Search
CPC .................................. A61B 10/0051
See application file for complete search history.

(56) References Cited

U.S. PATENT DOCUMENTS

| | | | |
|---|---|---|---|
| 5,266,266 A * | 11/1993 | Nason ............... | A61B 10/0096 604/3 |
| 5,910,122 A | 6/1999 | D'Angelo | |
| 8,202,230 B2 | 6/2012 | Gatzemeyer | |
| 8,647,115 B2 * | 2/2014 | Boehm ................ | A61C 5/62 433/90 |
| 9,932,622 B2 * | 4/2018 | Bayliff ............... | G01N 33/573 |
| 10,119,968 B2 * | 11/2018 | Lansing ............. | G01N 33/5302 |
| 10,413,384 B2 * | 9/2019 | Bublewitz .......... | B05C 17/00559 |
| 10,845,369 B2 * | 11/2020 | Bennion ............. | B01L 3/5023 |
| 10,851,404 B2 * | 12/2020 | Jiang ................. | B01L 3/5029 |
| 11,324,447 B2 | 5/2022 | Zegarelli | |
| 2002/0015663 A1 * | 2/2002 | Goldstein .......... | G01N 33/5302 436/164 |
| 2004/0152206 A1 * | 8/2004 | Davis ................. | A61B 10/0045 436/514 |
| 2005/0119589 A1 * | 6/2005 | Tung .................. | A61B 10/0045 600/584 |
| 2006/0039833 A1 * | 2/2006 | Yong .................. | B01L 3/502 73/864.91 |
| 2007/0025886 A1 * | 2/2007 | Yong .................. | B01L 3/502 422/400 |

(Continued)

FOREIGN PATENT DOCUMENTS

| | | |
|---|---|---|
| CA | 1322970 | 10/1993 |
| EP | 2670856 | 12/2013 |

(Continued)

*Primary Examiner* — May A Abouelela
(74) *Attorney, Agent, or Firm* — Nath, Goldberg & Meyer; Richard C. Litman

(57) ABSTRACT

The saliva collection kit includes a housing, a plunger, and a gum-like hydrogel that can be removably disposed in the housing. The housing is defined by a cylindrical barrel, which receives the plunger at one end and is connected to a hub at an opposing end. The hub includes an open free end and a cotton filter disposed within the hub. The gum-like hydrogel can be chewed to collect saliva in the mouth and disposed in the barrel after chewing. The hydrogel can then be compressed with the plunger to release purified saliva from the hydrogel into the hub. As the purified saliva flows through the hub, the cotton filter can further purify the saliva to provide a filtered saliva.

2 Claims, 2 Drawing Sheets

(56) References Cited

U.S. PATENT DOCUMENTS

| | | | |
|---|---|---|---|
| 2008/0058677 A1* | 3/2008 | Yong | A61B 10/0045 600/573 |
| 2009/0075289 A1* | 3/2009 | Zhang | C12Q 1/6806 435/6.14 |
| 2009/0143699 A1* | 6/2009 | Wu | A61B 10/0051 600/576 |
| 2009/0215159 A1* | 8/2009 | Kirby | B01L 3/502 435/287.7 |
| 2009/0269247 A1* | 10/2009 | Grenz | A61B 10/0051 422/400 |
| 2010/0311177 A1* | 12/2010 | Wu | B01L 3/5029 422/69 |
| 2011/0076776 A1 | 3/2011 | Ray | |
| 2011/0256531 A1 | 10/2011 | Raj | |
| 2014/0011162 A1* | 1/2014 | Zegarelli | A61K 9/0053 433/215 |
| 2014/0056830 A1* | 2/2014 | Pather | A61K 31/12 424/59 |
| 2016/0121322 A1* | 5/2016 | Fuller | B01L 3/5023 422/417 |
| 2016/0123856 A1* | 5/2016 | Slowey | C12N 15/1006 422/534 |
| 2017/0151260 A1* | 6/2017 | Hariharan | A61K 9/1075 |
| 2019/0086432 A1* | 3/2019 | Tran | G01N 33/497 |
| 2019/0219565 A1* | 7/2019 | Leung | G01N 33/6848 |
| 2020/0113550 A1* | 4/2020 | Sessions | A61B 10/0283 |
| 2020/0163656 A1 | 5/2020 | Orlin | |
| 2020/0253524 A1* | 8/2020 | Bullington | A61B 10/0051 |
| 2020/0397416 A1* | 12/2020 | Chronis | A61B 10/0051 |
| 2021/0137503 A1* | 5/2021 | Menon | A61B 5/4875 |
| 2021/0196246 A1* | 7/2021 | Wang | A61B 10/0051 |
| 2021/0215585 A1* | 7/2021 | Fruchter | G01N 1/4077 |
| 2021/0228190 A1* | 7/2021 | Fabrizio | A61B 5/150755 |
| 2021/0353268 A1* | 11/2021 | Gross | A61B 10/0051 |
| 2021/0355525 A1* | 11/2021 | Gjerde | C12Q 1/6806 |
| 2021/0387178 A1* | 12/2021 | Liew | A61B 10/007 |
| 2022/0031660 A1* | 2/2022 | Davies | A61K 31/404 |
| 2022/0061822 A1* | 3/2022 | Robbins | A61B 10/0051 |
| 2022/0071604 A1* | 3/2022 | Mide | B01L 3/5085 |
| 2022/0097073 A1* | 3/2022 | Prakash | B01L 3/5023 |
| 2022/0362303 A1* | 11/2022 | Playford | A61K 47/36 |
| 2023/0165269 A1* | 6/2023 | Phillips | C12Q 1/6806 424/48 |

FOREIGN PATENT DOCUMENTS

| | | |
|---|---|---|
| EP | 3328316 | 6/2018 |
| WO | 2022098730 | 5/2022 |
| WO | 2022189645 | 9/2022 |

\* cited by examiner

SALIVA COLLECTION KIT

BACKGROUND

1. Field

The disclosure of the present patent application relates to kits for collection of a biological sample, and particularly, to a saliva collection kit.

2. Description of the Related Art

Various tests are available that can be used to assess the presence of biological analytes in a sample. Such tests include tests based on the detection of microorganisms using microbiological culture techniques and tests based on detection of microorganisms using immunochemical techniques. Samples are typically obtained using either a swab device or by direct contact with a culture device such as an agar plate. The sample can be analyzed for the presence of live cells and, in particular, live microorganisms.

Saliva is a biofluid that can provide useful information on a person's genetics, health, and metabolism. For testing purposes, saliva must be purified from mucins and food particles typically present in the mouth. Prior devices generally require considerable handling of a saliva specimen before it is ready to be tested. This can result in contamination of the saliva specimen or the technician handling the specimen.

Thus, a saliva collection kit solving the aforementioned problems is desired.

SUMMARY

The saliva collection kit includes a housing, a plunger, and a gum-like hydrogel that can be removably disposed in the housing. In an embodiment, the kit is configured as a syringe-type structure, wherein the housing is defined by a cylindrical barrel that receives the plunger at one end and is connected to a hub at an opposing end. The hub includes an open free end and a cotton filter disposed within the hub. The gum-like hydrogel can be chewed to collect saliva in the mouth and disposed in the barrel after chewing. The hydrogel can then be compressed with the plunger to release purified saliva from the hydrogel into the hub. As the purified saliva flows through the hub, the cotton filter can further purify the saliva to provide a filtered saliva. The filtered saliva flowing out of the hub can be collected in a container. The container can include a solution to preserve the saliva.

These and other features will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
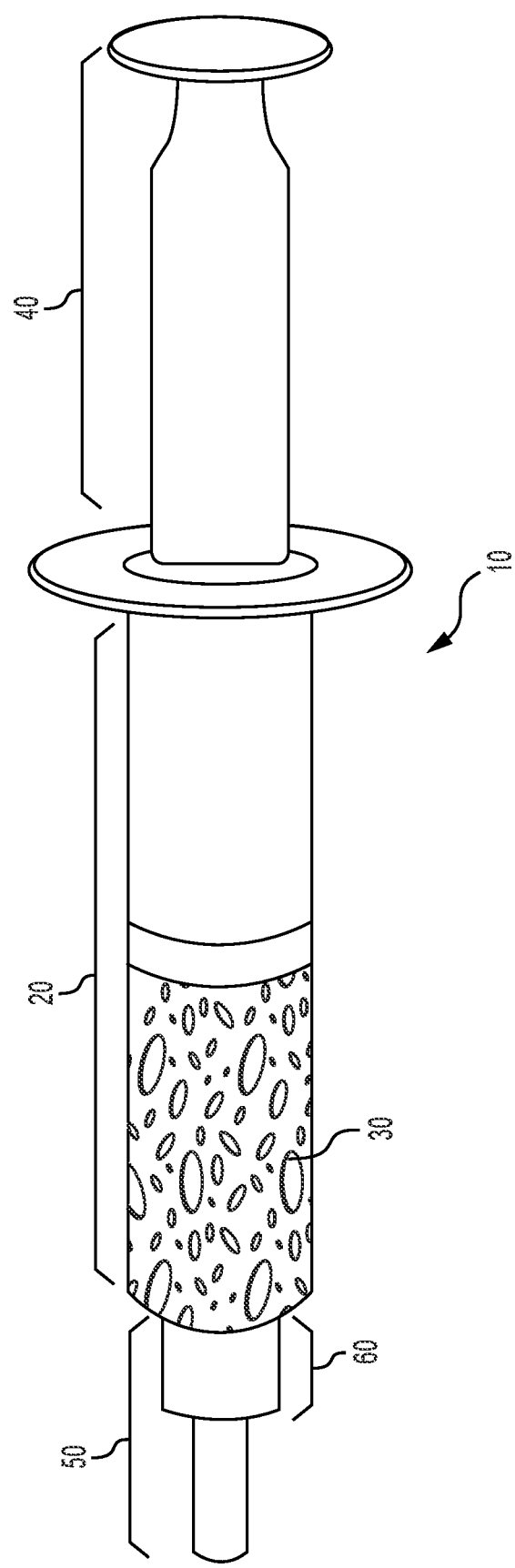
FIG. 1 is a perspective view of the saliva collection kit.

As shown in FIG. 1, a saliva collection kit 10 includes a housing including a barrel 20 and a hub 50, a plunger 40 configured for removable insertion in the barrel 20, and a gum-like hydrogel or hydrogel gum 30 that can be removably disposed in the barrel 20. In an embodiment, the kit 10 can be configured as a syringe-type structure, as shown in FIG. 1. Thus, the housing can be generally cylindrical with the diameter of the barrel 20 being larger than the diameter of the hub 50. The barrel 20 can removably receive the plunger 40 at one end. The hub 50 extends from an opposing end of the barrel 20. The hub 50 includes an open free end and a filter 60 disposed within the hub. The filter 60 can be formed from cotton or other suitable material.

The gum-like hydrogel 30 can be chewed to collect saliva in the mouth and placed in the barrel 20 after chewing. The hydrogel 30 can then be compressed with the plunger 40 to release purified saliva from the hydrogel 30 into the hub 50. As the purified saliva flows through the hub 50, the filter 60 can further purify the saliva to provide additional filtration of the saliva. The filtered saliva flowing out of the hub 50 can then be collected in a container. The container can include a solution to preserve the saliva.

The hydrogel 30 can be any suitable biocompatible, liquid-absorbing hydrogel 30 known in the art. The liquid-absorbing hydrogel 30 may be a naturally occurring or synthetic material that absorbs water or other liquid. The hydrogel 30 can retain a large amount of liquid without disintegrating or dissolving. In addition to retaining liquid, the hydrogel 30 can retain or adhere to mucins or food residue in the saliva. Exemplary hydrogels include, but are not limited to, maltodextrins, cetyl alcohol, chitosan, lecithins, polypeptides, waxes, and edible polymers.

Figure 2:
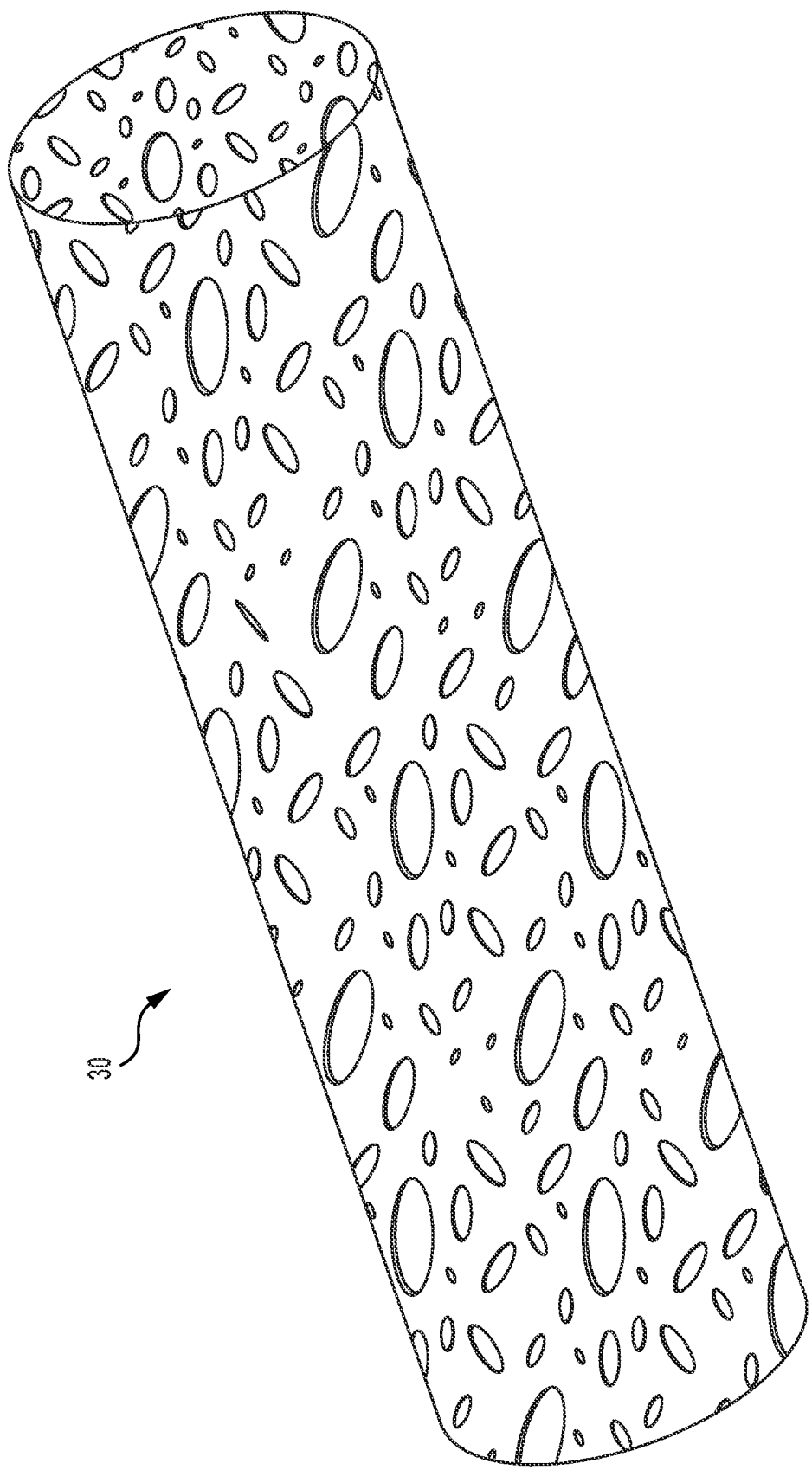
FIG. 2 is a perspective view of the hydrogel gum of the saliva collection kit.

The hydrogel 30 exhibits ductile properties so that, when chewed, the hydrogel 30 does not break down under repetitive stress. Although the hydrogel 30 shown in FIG. 2 is generally cylindrical, the hydrogel 30 can be molded into a variety of shapes to provide good strength and stiffness and other desired physical properties to enhance functionality and chewing enjoyment.

The hydrogel 30 can be chewed to collect saliva in the mouth. After chewing, the hydrogel 30 can be placed in the barrel 20 and compressed in the barrel 20 using the plunger 40. Compressing the hydrogel 30 can cause liquid retained in the hydrogel 30 to be released into the barrel 20 while allowing mucin and/or food particles to remain attached to the hydrogel 30. Once the liquid is transferred to the barrel 20, the liquid can flow into the hub 50. The filter 60 in the hub 50 can further purify the saliva before the saliva flows out of the hub 50. The saliva can be collected in a suitable container. Preferably, the container is provided with a solution to preserve the saliva.

It is to be understood that the saliva collection kit is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. 1. A saliva collection kit, consisting essentially of:
   a housing;
   a plunger configured for removable insertion in the housing; and
   a hydrogel gum configured for removable insertion in the housing, the hydrogel gum being adapted for retaining the saliva after being chewed;
   wherein the housing comprises a barrel and a hub extending from one end of the barrel, the barrel having a diameter larger than the hub;

wherein the hub includes a filtration material disposed therein;
wherein the filtration material is formed from cotton;
wherein the cotton filtration material retains mucins and food particles;
wherein the hydrogel gum is selected from the group consisting of maltodextrins, cetyl alcohol, chitosan, lecithins, polypeptides, waxes, and edible polymers; and
wherein the hydrogel gum absorbs liquid and retains an amount of liquid without disintegrating or dissolving.

2. A saliva collection kit, consisting essentially of:

a generally cylindrical housing including a barrel and a hub, the barrel having a diameter larger than the hub;

a plunger configured for removable insertion in the barrel; and a hydrogel gum configured for removable insertion in the barrel, the hydrogel gum being adapted for retaining the saliva after being chewed;

wherein the hub includes a filtration material; and
wherein the filtration material is formed from cotton;
wherein the cotton filtration material retains mucins and food particles;
wherein the hydrogel gum is selected from the group consisting of maltodextrins, cetyl alcohol, chitosan, lecithins, polypeptides, waxes, and edible polymers; and
wherein the hydrogel gum absorbs liquid and retains an amount of liquid without disintegrating or dissolving.

\* \* \* \* \*